(12) United States Patent
Pak et al.

(10) Patent No.: US 10,591,523 B2
(45) Date of Patent: Mar. 17, 2020

(54) CAPACITIVE SENSOR AND MANUFACTURING METHOD THEREOF

(71) Applicant: Korea University Research and Business Foundation, Seoul (KR)

(72) Inventors: James Jungho Pak, Seoul (KR); Dae Seok Na, Daegu (KR)

(73) Assignee: Korea University Research and Business Foundation, Seoul (KR)

( * ) Notice: Subject to any disclaimer, the term of this patent is extended or adjusted under 35 U.S.C. 154(b) by 3 days.

(21) Appl. No.: 15/507,143

(22) PCT Filed: May 26, 2015

(86) PCT No.: PCT/KR2015/005222
§ 371 (c)(1),
(2) Date: Feb. 27, 2017

(87) PCT Pub. No.: WO2016/032093
PCT Pub. Date: Mar. 3, 2016

(65) Prior Publication Data
US 2017/0276711 A1   Sep. 28, 2017

(30) Foreign Application Priority Data

Aug. 29, 2014  (KR) .................. 10-2014-0113951
Dec. 5, 2014  (KR) .................. 10-2014-0173486

(51) Int. Cl.
*G01R 27/26* (2006.01)
*G01D 5/24* (2006.01)
*G01N 33/30* (2006.01)
*H01L 21/306* (2006.01)
*H01L 21/31* (2006.01)

(52) U.S. Cl.
CPC .......... *G01R 27/2605* (2013.01); *G01D 5/24* (2013.01); *G01D 5/2405* (2013.01); *G01N 33/30* (2013.01); *H01L 21/306* (2013.01); *H01L 21/31* (2013.01)

(58) Field of Classification Search
CPC ... G01R 27/2605; H01L 21/31; H01L 21/306; G01D 5/24; G01N 33/30
See application file for complete search history.

(56) References Cited

U.S. PATENT DOCUMENTS

| | | | |
|---|---|---|---|
| 2008/0180883 A1* | 7/2008 | Palusinski | ................ H01G 4/06 361/524 |
| 2009/0273356 A1* | 11/2009 | Pampin | ................ C12Q 1/6816 324/693 |
| 2014/0015548 A1* | 1/2014 | Naughton | ............. G01R 27/26 324/658 |

(Continued)

FOREIGN PATENT DOCUMENTS

| KR | 100511268 B1 | 8/2005 |
|---|---|---|
| KR | 100561908 B1 | 3/2006 |

(Continued)

*Primary Examiner* — Akm Zakaria
(74) *Attorney, Agent, or Firm* — NSIP Law

(57) ABSTRACT

A capacitive sensor is disclosed. The capacitive sensor includes a substrate, a first electrode and a second electrode formed on the substrate, an insulation layer formed on the substrate on which the first electrode and the second electrode are formed, and a sensing layer that is formed on the insulation layer and includes graphene.

13 Claims, 10 Drawing Sheets

(56) References Cited

U.S. PATENT DOCUMENTS

| | | | |
|---|---|---|---|
| 2014/0103296 A1* | 4/2014 | Yu | G01N 27/127 |
| | | | 257/29 |
| 2014/0145735 A1* | 5/2014 | Koester | G01N 27/227 |
| | | | 324/686 |
| 2014/0184527 A1* | 7/2014 | Kim | G06F 3/044 |
| | | | 345/173 |
| 2017/0350846 A1* | 12/2017 | Cook | G01N 27/223 |

FOREIGN PATENT DOCUMENTS

| KR | 20060062437 A | 6/2006 |
|---|---|---|
| KR | 100618627 B1 | 9/2006 |
| KR | 100625608 B1 | 9/2006 |
| KR | 20110049593 A | 5/2011 |
| KR | 20140061278 A | 5/2014 |

* cited by examiner

CAPACITIVE SENSOR AND MANUFACTURING METHOD THEREOF

CROSS-REFERENCE TO RELATED APPLICATIONS

This application is the U.S. National Phase of International Application No. PCT/KR2015/005222, filed May 26, 2015, which claims priority to Korean Patent Application No. 10-2014-0113951, filed Aug. 29, 2014 and Korean Patent Application No. 10-2014-0173486, filed Dec. 5, 2014, the disclosures of which are incorporated herein by reference in their entirety.

TECHNICAL FIELD

The present disclosure relates to a capacitive sensor, more particularly to a capacitive sensor and a method of manufacturing the capacitive sensor with which the electrical properties of a measurement target or changes in the electrical properties of a measurement target can be measured using a sensing layer that contains graphene.

BACKGROUND

The degradation of a measurement target, such as engine oil used in vehicles for instance, may result from a variety of physical and chemical causes. In most cases, however, a user would determine when to change engine oil based only on the viscosity of the engine oil or a change in its color. Recently, it was discovered that there is a close relationship between the degradation of engine oil and changes in the permittivity or electrical conductivity of the engine oil, both of which are electrical properties of the engine oil. As such, studies are being conducted that aim to sense the state of engine oil by measuring the electrical properties of the engine oil. While certain studies have used output voltage, AC impedance, or viscosity, from among the electrical properties of the engine oil, the results as yet cannot satisfy user demands in terms of reliability, durability, and response speed.

Changes in the dielectric constant of engine oil may result from various physical and chemical changes in the engine oil and enable the observer to easily obtain information on changes in the engine oil. However, measurement devices using the dielectric constant that have been developed until now are of a cylindrical form or a parallel plate form of a relatively large volume and as such face problems in mass production and implementing miniaturized sizes.

SUMMARY

The present solution relates to a capacitive sensor and a method of manufacturing a capacitive sensor with which the electrical properties of a measurement target or changes in the electrical properties of a measurement target can be measured with high sensitivity.

In some scenarios, the capacitive sensor includes a substrate, a first electrode and a second electrode formed on the substrate, an insulation layer formed on the substrate on which the first electrode and the second electrode are formed, and a sensing layer that is formed on the insulation layer and includes graphene.

In those or other scenarios, the method of manufacturing a capacitive sensor includes forming at least one electrode on a substrate, forming an insulation layer on the substrate on which the at least one electrode is formed, and forming a sensing layer that includes graphene on the insulation layer.

The capacitive sensor according to the present solution makes it possible to measure the electrical properties of a measurement target or changes in the electrical properties of a measurement target with high sensitivity.

DETAILED DESCRIPTION

Figure 1:
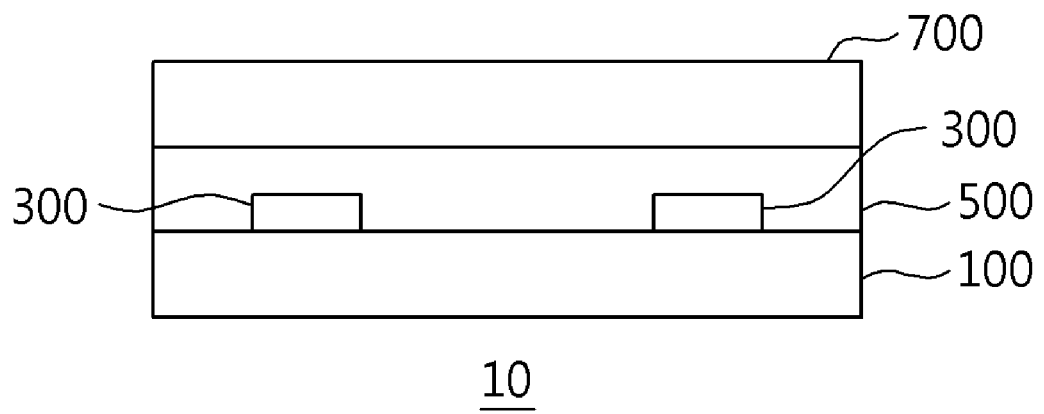
FIG. 1 illustrates a capacitive sensor.

Descriptions of specific structures or functions relating to certain embodiments derived based on the concept of the present invention as set forth in the present specification are provided merely as examples for explaining the embodiments derived from the concept of the invention. The embodiments can be practiced in a variety of implementations and are not limited to the embodiments described herein.

As the embodiments derived from the concept of the present invention allow for various modifications and can be implemented in various forms, certain embodiments are illustrated in the drawings and described in detail in the present specification. However, this is not intended to limit the embodiments derived from the concept of the invention to the specific disclosed forms, and it is to be appreciated that all modifications, equivalents, and substitutes that do not depart from the spirit and technical scope of the present invention are encompassed in the present invention.

While such terms as "first" and "second," etc., may be used to describe various components, such components must not be limited to the above terms. The above terms are used only to distinguish one component from another. For example, a first component may be referred to as a second component without departing from the scope of rights of the present invention, and likewise a second component may be referred to as a first component.

When a component is mentioned to be "connected" or "joined" to another component, this may mean that it is directly connected or joined to the other element, but it is to be understood that yet another component may exist in-between. On the other hand, when a component is mentioned to be "directly connected" or "directly joined" to another component, it is to be understood that there are no other components in-between. The same applies to other expressions describing the relationships of components, such as "between" and "immediately between" or "neighboring" and "directly neighboring".

The terms used in the present specification are merely used to describe particular embodiments, and are not intended to limit the present invention. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Unless otherwise defined, all terms used herein, including technical or scientific terms, have the same meanings as those generally understood by those with ordinary knowledge in the field of art to which the present invention pertains. Such terms as those defined in a generally used dictionary are to be interpreted to have the meanings equal to the contextual meanings in the relevant field of art, and are not to be interpreted to have ideal or excessively formal meanings unless clearly defined in the present specification.

Certain embodiments of the invention will be described below in more detail with reference to the accompanying drawings.

FIG. 1 illustrates a capacitive sensor according to the present solution.

Referring to FIG. 1, a capacitive sensor 10 may include a substrate 100, at least one electrode 300, an insulation layer 500, and a sensing layer 700.

The substrate 100 can include glass or silicon. In some scenarios, the substrate 100 can be implemented as an alumina substrate that contains alumina. In cases where the substrate 100 is implemented with silicon, it can be necessary to implement an additional oxide layer or insulation layer between the substrate 100 and the at least one electrode 300.

At least one electrode 300 may be formed on the substrate 100. The at least one electrode 300 can be implemented in a particular pattern. At least one electrode 300 can contain at least one or more type of an electrical conductor, such as a metallic substance such as chromium (Cr), gold (Au), aluminum (Al), platinum (Pt), molybdenum (Mo), iron (Fe), copper (Cu), tungsten (W), palladium (Pd), etc., for example. In some scenarios, at least one electrode 300 can also be implemented as a transparent electrode that contains ITO (indium tin oxide), graphene, etc. A power supply having a frequency of 100 Hz to 10 kHz can be applied to at least one electrode 300, but the present solution is not limited to frequencies of a particular range as regards the power supply applied to the at least one electrode 300.

The insulation layer 500 may be formed on the substrate 100, on which at least one electrode 300 is formed. That is, the insulation layer 500 may be formed over portions of the substrate 100 on which the at least one electrode 300 is not formed and over the at least one electrode 300. The insulation layer 500 can be implemented as an oxide or a nitride.

The sensing layer 700 may be formed on the insulation layer 500. The sensing layer 700 may include graphene. Graphene is a substance having a thickness equivalent to a single layer of atoms, formed as carbon atoms form a honeycomb-shaped lattice via sp2 bonding in two dimensions. Not only is graphene very stable both structurally and chemically, but also it enables the manufacture of a high-sensitivity capacitive sensor 10 if the edge structure of a graphene nanoribbon is used.

In some scenarios, the sensing layer 700 can also be implemented as graphene paste that contains graphene. The sensing layer 700 may have its electrical properties changed according to the state of the measurement target, such as engine oil for example, touched by the sensing layer 700. The electrical properties can include capacitance (also referred to as electrical capacity), permittivity, or the dielectric constant. The graphene paste can be implemented with a thickness of 5 μm to 10 μm, but the scope of the present solution is obviously not to be limited by the thickness of the graphene paste, and the thickness of the graphene paste after sintering can be within a range of 4 μm to 6 μm.

Thus, the capacitive sensor 10 can determine the state of the measured target substance by using a sensing layer 700 of which the electrical properties are changed according to the state of the measured target substance.

Figure 2:
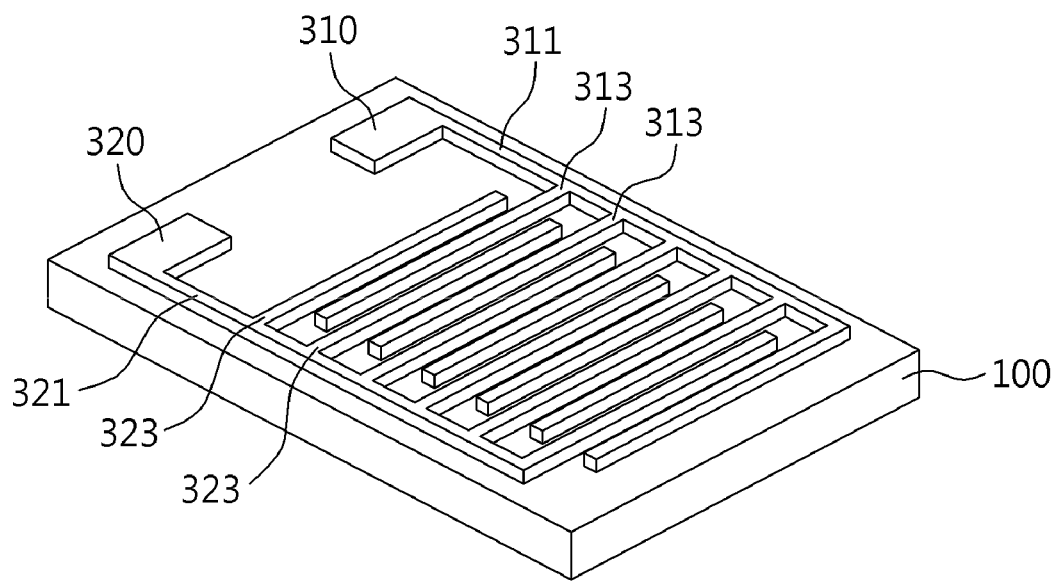
FIG. 2 illustrates the at least one electrode shown in FIG. 1.

FIG. 2 illustrates the at least one electrode shown in FIG. 1.

Referring to FIG. 1 and FIG. 2, the at least one electrode 300 may include a first electrode 310 and a second electrode 320. The first electrode 310 and the second electrode 320 can be implemented as interdigit electrodes. The pattern formed by the first electrode 310 and second electrode 320 implemented as interdigit electrodes can be described with the following exemplary implementation. However, the configurations and forms of the first electrode 310 and second electrode 320 are not to be limited to the below described exemplary implementation, and the first electrode 310 and second electrode 320 can also be implemented as interdigit electrodes having polygonal shapes, including circular shapes, triangular shapes, quadrilateral shapes, and so on.

The first electrode 310 may include a first extending part 311 that extends along a first direction, such as the lengthwise direction (or widthwise direction) of the substrate 100 for example, and a multiple number of first branch parts 313 that protrude from the first extending part 311 along a second direction, such as the widthwise direction (or lengthwise direction) of the substrate 100 for example. Here, the second direction and the first direction can form a perpendicular angle or form a predetermined angle. In some examples, the first electrode 310 and the second electrode 320 can be implemented as interdigit electrodes having sawtooth-like configurations.

The second electrode 320 may include a second extending part 321 that extends along an opposite direction of the first direction or along the first direction and a multiple number of second branch parts 323 that protrude from the second extending part 321 along an opposite direction of the second direction. Since the second direction is a direction facing the second electrode 320, the first branch parts 313 and the second branch parts 323 can be arranged in a staggered manner.

Also, the width of the first electrode 310 and the width of the second electrode 320, especially the widths of the first branch parts 313 and the widths of the second branch parts 323, can be implemented to be smaller than or equal to 100 μm, and the gap between the first electrode 310 and the second electrode 320, especially the gap between the first branch parts 313 and the second branch parts 323 can be implemented to be smaller than or equal to 100 μm. Of course, the present solution is not limited to certain values in terms of electrode widths or electrode gaps.

By implementing a particular pattern, such as that described above, for the first electrode 310 and second electrode 320, the electrodes facing each other can be given larger surface areas, whereby the sensitivity of the capacitive sensor 10 can be greatly improved.

FIG. 3A, FIG. 3B, FIG. 3C, and FIG. 3D illustrate a method of manufacturing the capacitive sensor shown in FIG. 1.

Figure 3A:
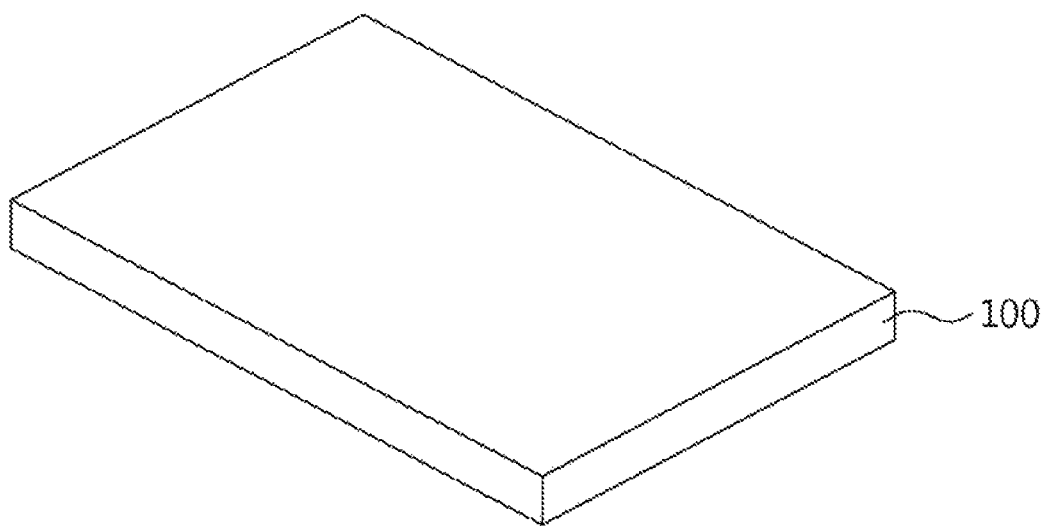
FIGS. 3A, 3B, 3C and 3D illustrate a method of manufacturing the capacitive sensor shown in FIG. 1.

As illustrated in FIG. 3A, a substrate 100 for manufacturing a capacitive sensor may be prepared.

Figure 3B:
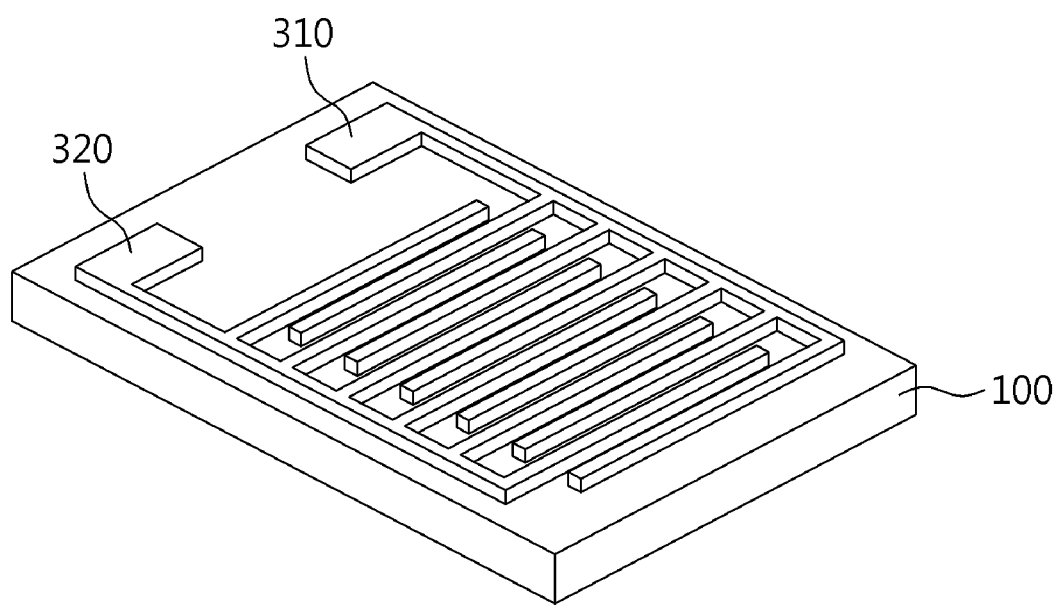

As illustrated in FIG. 3B, at least one electrode 310, 320 may be formed on the substrate 100. In order to form at least one electrode 310, 320, an electrode substance may first be deposited on the substrate 100. The electrode substance can include at least one or more of a metallic substance such as chromium (Cr), gold (Au), aluminum (Al), platinum (Pt), molybdenum (Mo), copper (Cu), iron (Fe), tungsten (W), palladium (Pd), etc. Also, the electrode substance can be formed by PVD (physical vapor deposition), which may include evaporation, sputtering, etc., or by CVD (chemical vapor deposition). In some scenarios, the electrode substance can also be formed by a printing technique.

For forming at least one electrode 310, 320 of a particular pattern from the electrode substance, a lithography process may be performed, which may include the processes of coating a photosensitive material, exposure to light, and etching. It is possible to form the at least one electrode 310, 320 having a particular pattern by depositing the electrode substance on the substrate 100 and performing a lithography process on the deposited electrode substance.

Figure 3C:
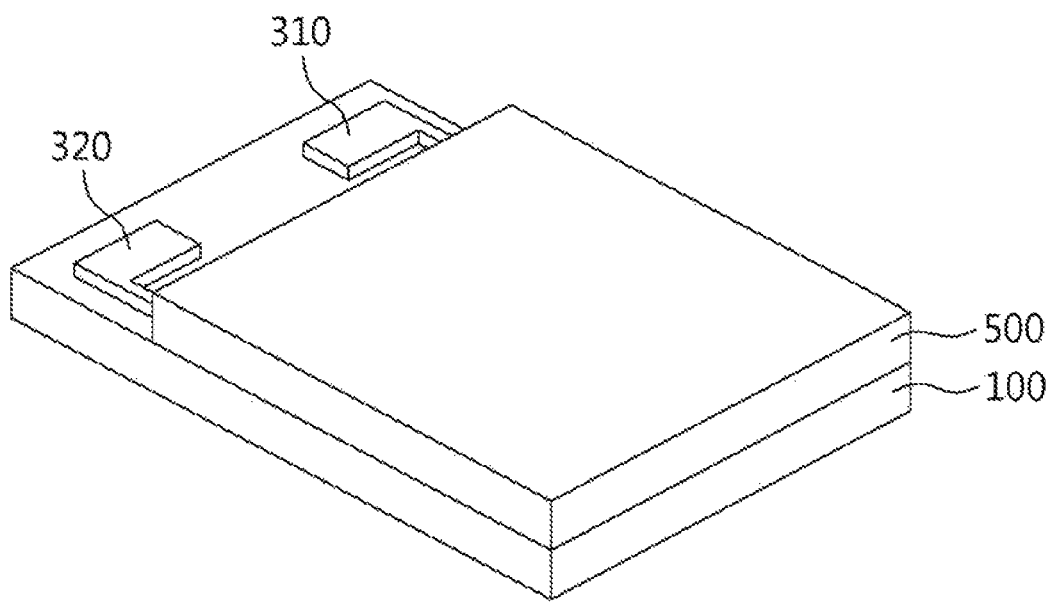

As illustrated in FIG. 3C, an insulation layer 500 may be formed on the substrate 100 having at least one electrode 310, 320 formed thereon. The insulation layer 500, which can be implemented as a nitride or an oxide, can be formed by PVD, such as by evaporation, sputtering, etc., or by CVD. In some scenarios, the electrode substance can also be formed by a printing technique.

Here, the insulation layer 500 can also be formed on only a portion of the substrate 100, but this portion may include at least the portions where the pattern of the first electrode 310, i.e. the pattern of the first extending part 311 and the first branch parts 313, and the pattern of the second electrode 320, i.e. the second extending part 321 and the second branch parts 323, are formed.

Regarding the thickness of the insulation layer 500, it was observed in experiments that if the insulation layer 500 is thicker than 1000 Å, the initial capacitance value of the capacitive sensor 10 is decreased, and that when the thickness of the insulation layer 500 is 2000 Å, its sensitivity is decreased in half compared to when the thickness is 1000 Å. Also, if the thickness of the insulation layer 500 is smaller than or equal to 500 Å, the insulation layer 500 may not sufficiently cover the electrodes, and the sensing layer 700 formed on the insulation layer 500 may form a connection with the electrodes, resulting in a sensor that operates by measuring resistance, instead of a sensor that can measure permittivity by using a dielectric. Therefore, it may be desirable to form the insulation layer 500 with a thickness of 500 Å to 2000 Å, more desirably with a thickness of 1000 Å to 2000 Å. However, the present solution is not limited in scope by the thickness of the insulation layer 500.

Figure 3D:
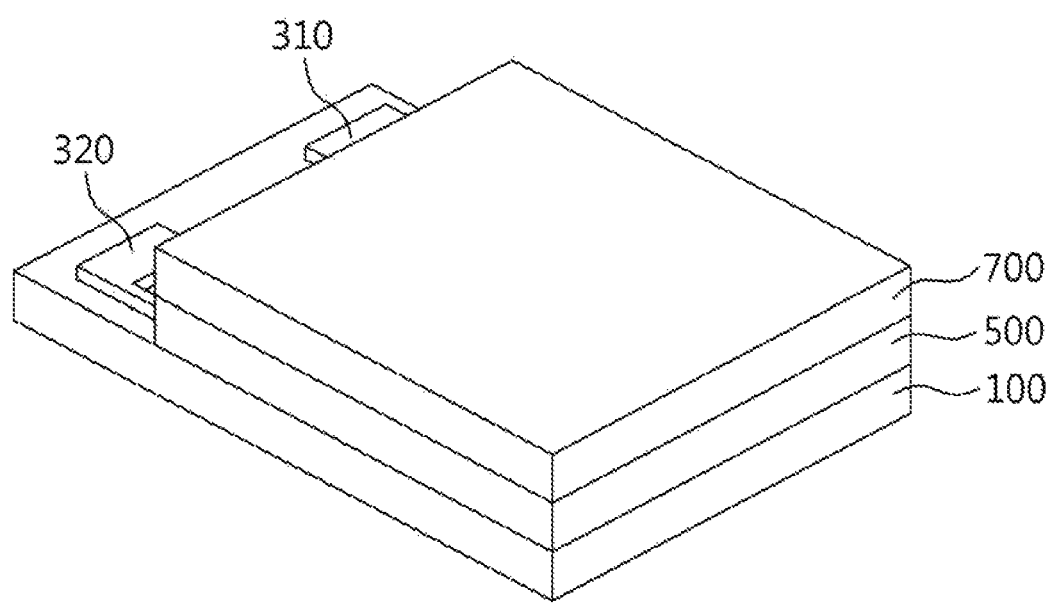

As illustrated in FIG. 3D, a sensing layer 700 may be formed on the insulation layer 500. The sensing layer 700, which can be implemented with graphene paste, can be formed by a screen printing technique or a coating technique. Also, since the sensitivity of the capacitive sensor 10 can change according to the area of the sensing layer 700 formed on the insulation layer 500, the sensing layer 700 can also be formed only on a portion of the insulation layer 500.

The graphene paste can be manufactured by a method that includes the operations of mixing a binder with alpha-terpineol and heating to a temperature of about 60° C. to melt the mixture, mixing graphene into a substance obtained by mixing glass frits with alpha-terpineol and applying heat for melting, screen printing the graphene paste and sintering, but the present solution is not limited thus. Here, in the operation of mixing in the graphene to the substance obtained by mixing glass frits with alpha-terpineol and applying heat for melting, the proportion of the binder and glass frits can be 4 weight % (tolerance range±2%). A capacitive sensor 10 that includes a graphene paste manufactured by the procedures above can have a high initial capacitance value and may not require a separate protective layer. This is because the graphene paste itself may serve as a protective layer.

Figure 4:
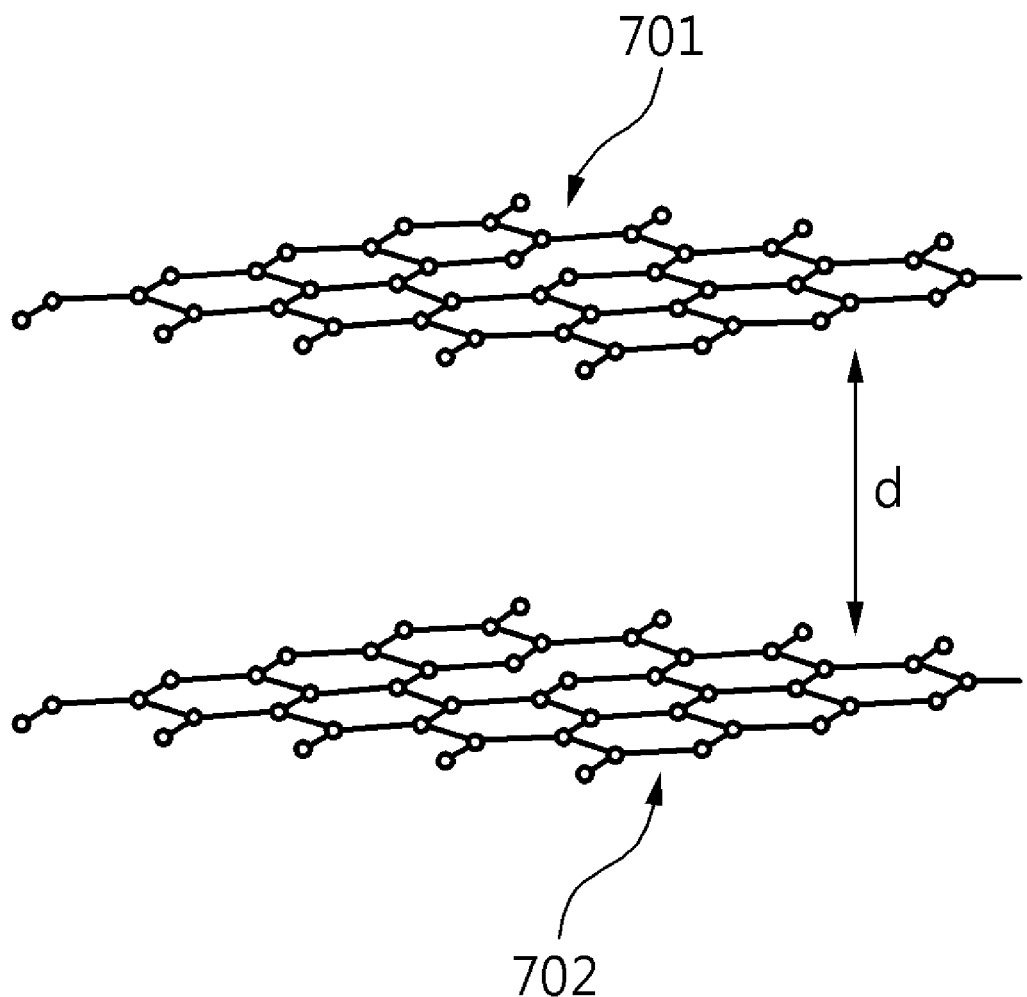
FIG. 4 illustrates the principle by which the electrical property of the sensing layer shown in FIG. 1 is changed.

FIG. 4 illustrates the principle by which the electrical property of the sensing layer shown in FIG. 1 is changed.

Referring to FIG. 4, the sensing layer 700 can include multiple graphene particles, but FIG. 4 only shows two neighboring graphene particles 701, 702.

When a power supply is applied to the first electrode 310 and second electrode 320, the amount of ions that adhere to the graphene particles may change, resulting in a change in the capacitance (or permittivity) of the sensing layer 700.

When the distance between a first graphene particle 701 and a second graphene particle 702 is d, a small capacitance is obtained between the first graphene particle 701 and the second graphene particle 702. The first graphene particle 701 can be adjacent to multiple graphene particles other than the second graphene particle 702, and the capacitance obtained with respect to the first graphene particle 701 can be considered the total of the small capacitances created between the first graphene particle 701 and the multiple adjacent graphene particles or of the small capacitances created between the first graphene particle 701 and all of the graphene particles included in the sensing layer 700.

In this way, the capacitance of each of the graphene particles included in the sensing layer 700 can be considered, and the capacitance of the sensing layer 700 can be the sum of the capacitances of the multiple number of graphene particles.

The sensing layer 700 can be implemented with graphene paste, and numerous graphene particles can be included in the graphene paste, so that a capacitive sensor 10 having a high initial capacitance value can be fabricated. That is, in cases where graphene paste is not used, the initial capacitance from just the electrodes would range between several and several tens of pF, and such low initial capacitance would provide low sensitivity for the sensor. In contrast, in cases where graphene paste is used, the initial capacitance can reach several hundred pF, such as 300 pF or higher for example, providing improved sensitivity for the sensor.

Figure 5:
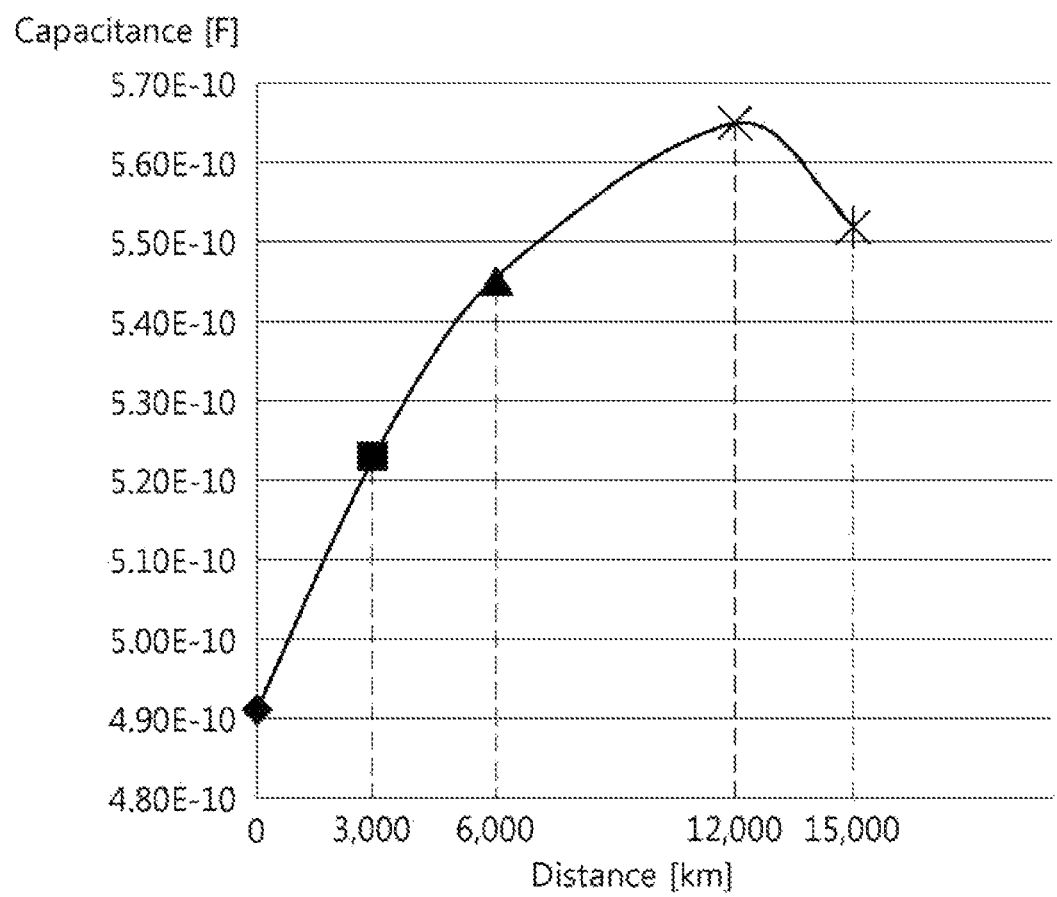
FIG. 5 and FIG. 6 are graphs representing changes in the capacitances of measurement targets measured using the capacitive sensor shown in FIG. 1.
Figure 6:
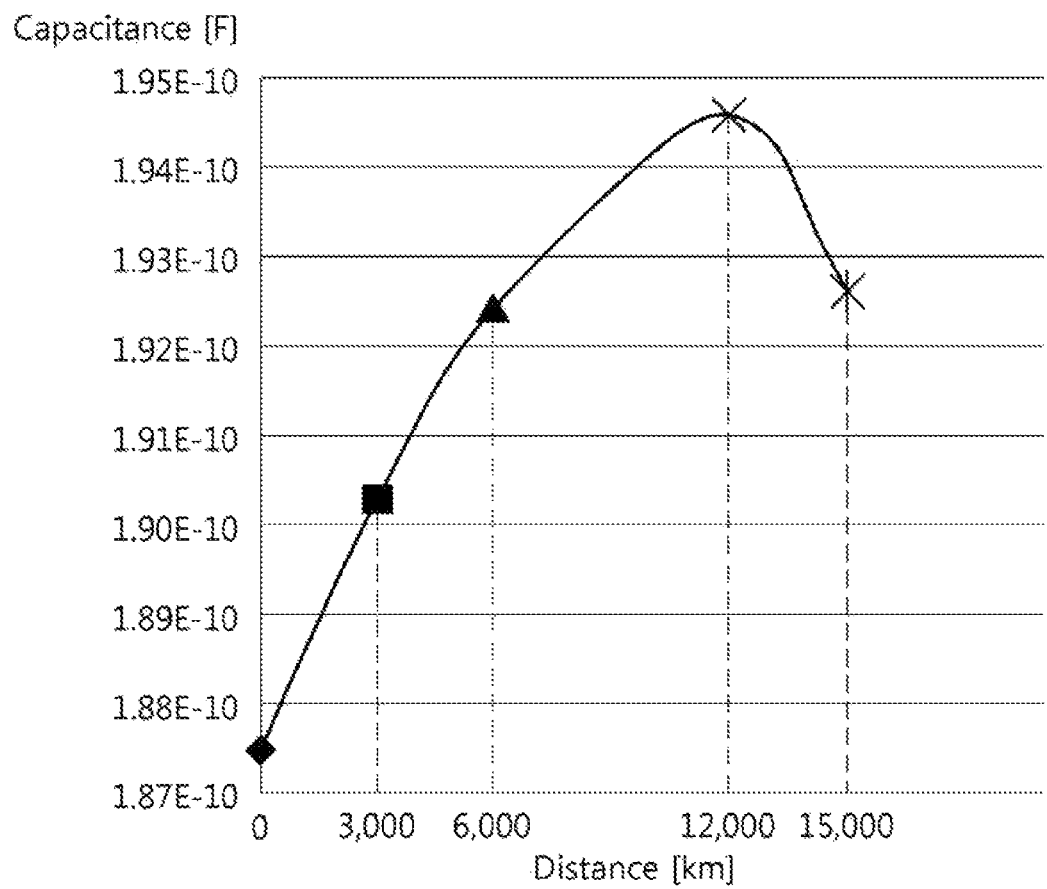
Figure 7:
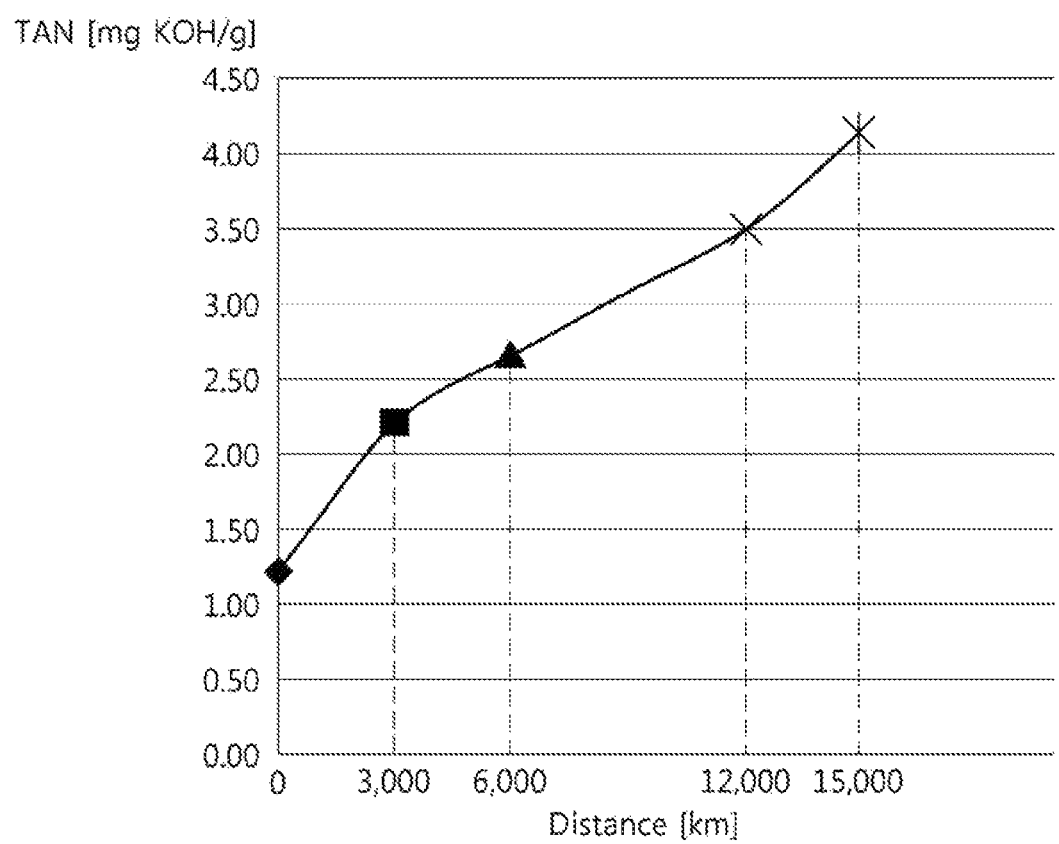
FIG. 7 is a graph representing changes in the total acid number of a measurement target.

FIG. 5 and FIG. 6 are graphs representing changes in the capacitances of measurement targets measured using the capacitive sensor shown in FIG. 1, and FIG. 7 is a graph representing changes in the total acid number of a measurement target.

Before the measurement, the capacitive sensor 10 illustrated in FIG. 1 was manufactured by forming a substrate 100 using glass, forming electrodes 300 having widths of 15 μm and a gap of 15 μm using 500 Å of chromium (Cr) and 500 Å of gold (Au), forming an insulation layer 500 using 3000 Å of silicon dioxide, applying a graphene paste by using a screen printing technique, and sintering the graphene paste. The initial capacitance of the capacitive sensor 10 manufactured by the procedures above is about 300 pF at ordinary temperature under an atmosphere.

The graph shown in FIG. 5 represents changes in the capacitance of a measurement target, for example engine oil, according to driving distance. A power supply of 100 Hz was applied to engine oil having a temperature of 80° C., and changes in the capacitance of the engine oil were measured. The capacitance values for various driving distances (0 km, 3000 km, 6000 km, 12000 km, and 15000 km) were measured as 490 pF, 523 pF, 545 pF, 565 pF, and 552 pF, respectively, showing an overall change of 75 pF.

The graph shown in FIG. 6 represents changes in the capacitance of a measurement target, for example engine oil, according to driving distance. A power supply of 10 Hz was applied to engine oil having a temperature of 80° C., and changes in the capacitance of the engine oil were measured. The capacitance values for various driving distances (0 km, 3000 km, 6000 km, 12000 km, and 15000 km) were measured as 187 pF, 190 pF, 192 pF, 194 pF, and 193 pF, respectively, showing an overall change of 6 pF.

The graph shown in FIG. 7 represents changes in the total acid number of a measurement target, for example engine oil, according to driving distance. The total acid number values for various driving distances (0 km, 3000 km, 6000 km, 12000 km, and 15000 km) were measured as 1.24, 2.20, 2.66, 3.51, and 4.12 (unit: mg KOH/g), respectively, showing an overall change of 2.88.

Looking at the changes in capacitance values shown in FIG. 5 and FIG. 6 and the changes in total acid number values shown in FIG. 7, it can be seen that the more the driving distance is increased, the more the total acid number is increased, and also the more the capacitance is increased for the engine oil. Thus, changes in the properties of the engine oil can be measured using the capacitive sensor 10.

In particular, when the total acid number becomes 4 or higher, it is observed that the value of the capacitance begins to decrease. This is in accordance with standards for measuring the service limit of engine oil which specify that engine oil should be changed when the total acid number changes by 2.0 or more compared to new oil. From the above, it is noted that a capacitive sensor based on the present solution can provide the advantage of allowing the user to determine when to change engine oil. The user can simply measure the output value of the capacitive sensor 10 and can determine that the engine oil may be changed after the measured output value begins to decrease, without having to install a particular device or program on the capacitive sensor 10.

Figure 8:
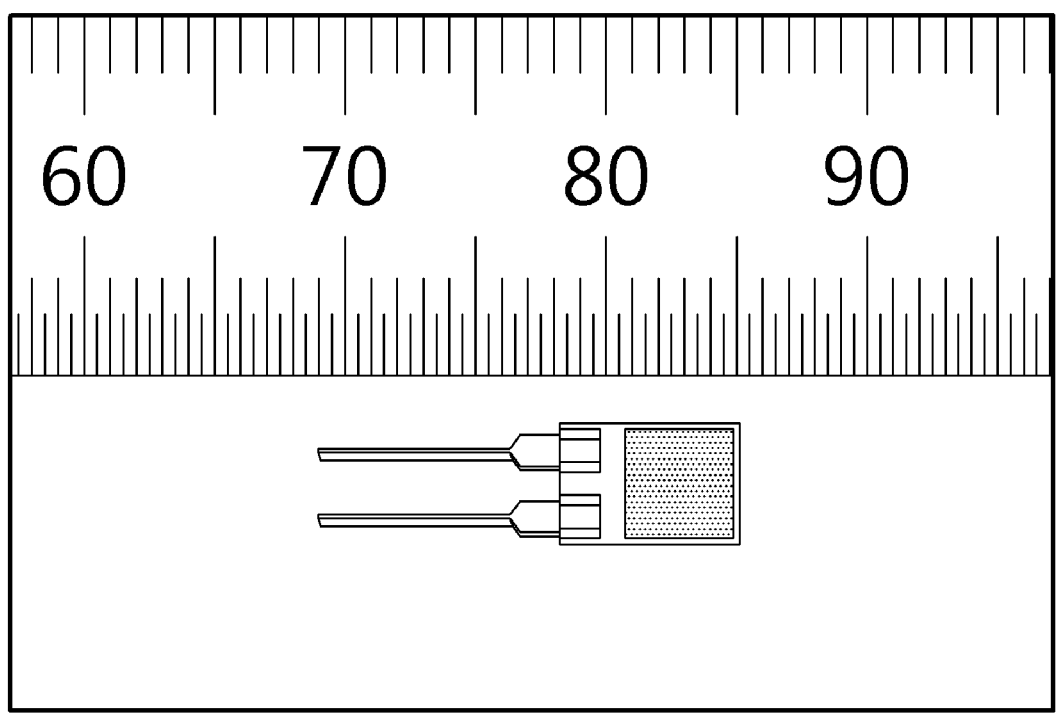
FIG. 8 illustrates a prototype of the capacitive sensor shown in FIG. 1.

FIG. 8 illustrates a prototype of the capacitive sensor shown in FIG. 1. By using a method of manufacturing a capacitive sensor according to the present solution as described above to produce a capacitive sensor, it is possible to produce a capacitive sensor that provides high response speed, excellent sensitivity, and high reliability in a miniaturized size, as illustrated in FIG. 8, with the added advantage that the capacitive sensor can be mass-produced with low costs.

To observe changes in the initial capacitance values according to the frequency of the power supply applied to the electrodes of the capacitive sensor, three samples were fabricated and their initial capacitance values measured, as shown in Table 1 below.

TABLE 1

| Frequency | 100 Hz | 1 kHz | 10 kHz | 100 kHz |
|---|---|---|---|---|
| Sample 1 | 462 pF | 348 pF | 182 pF | 108 pF |
| Sample 2 | 453 pF | 338 pF | 178 pF | 113 pF |
| Sample 3 | 448 pF | 343 pF | 193 pF | 121 pF |

From Table 1, it can be seen that the higher the frequency of the power supply applied to the electrodes, the lower are the initial capacitance values of the capacitive sensors. Also, it can be seen that, in order for a capacitive sensor to have an initial capacitance value of several hundred pF, a power supply having a frequency of 100 kHz or lower, preferably 10 kHz or lower, would be needed.

Figure 9:
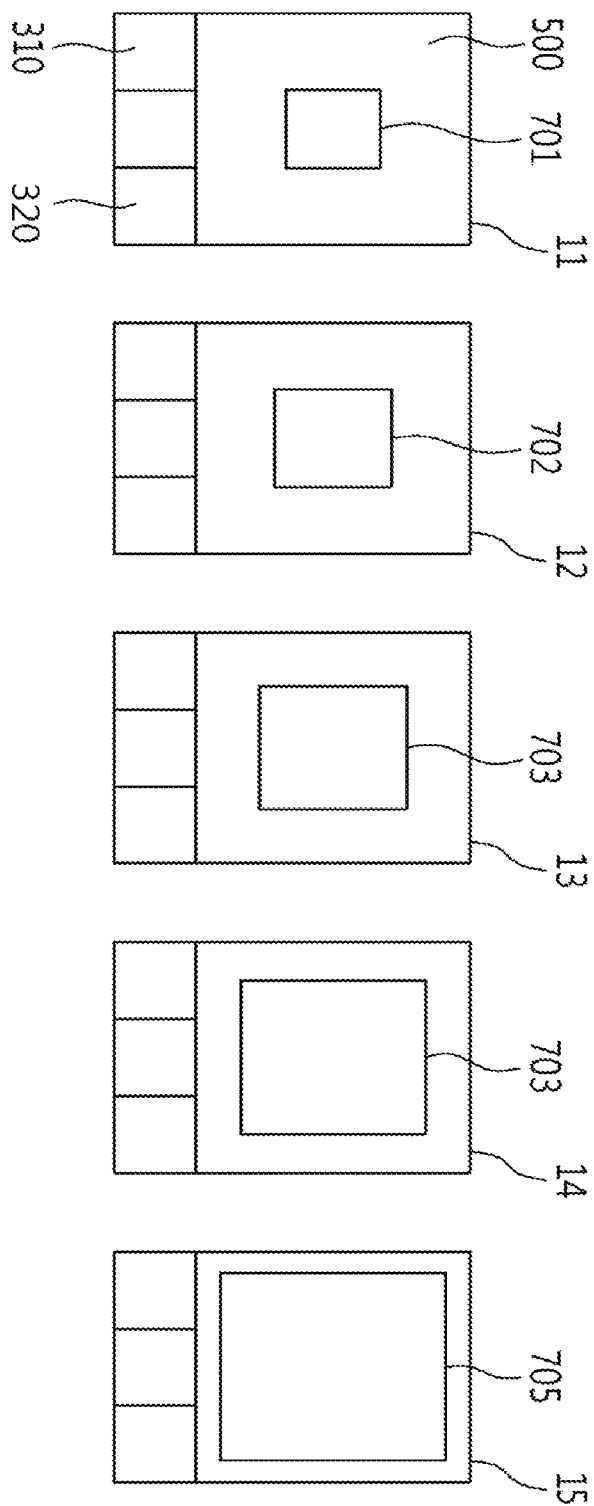
FIG. 9 illustrates samples fabricated for measuring the initial capacitance values of capacitive sensors according to the area of the sensing layer.
Figure 10:
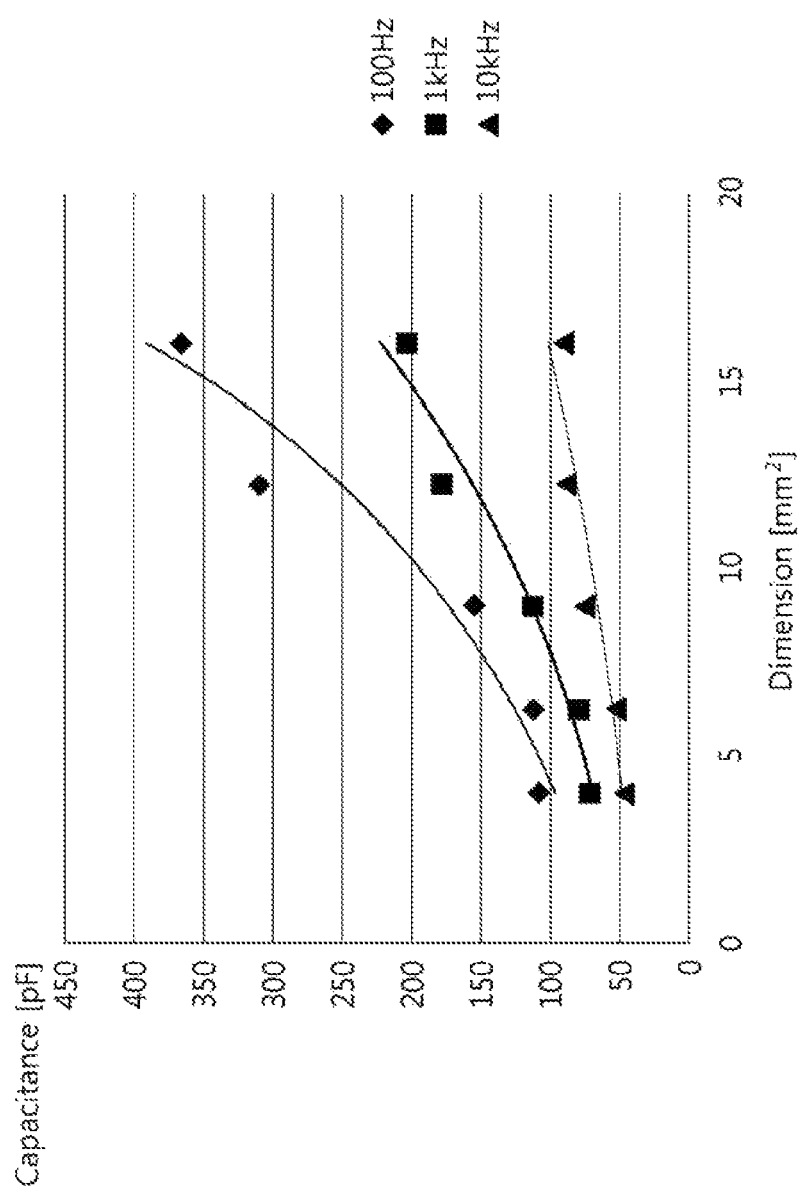
FIG. 10 is a graph representing changes in the initial capacitance values of the samples shown in FIG. 9.

FIG. 9 illustrates samples fabricated for measuring the initial capacitance values of capacitive sensors according to the area of the sensing layer, and FIG. 10 is a graph representing changes in the initial capacitance values of the samples shown in FIG. 9.

Referring to FIG. 9 and FIG. 10, a total of five samples 11 to 15 were fabricated for measuring the initial capacitance values of capacitive sensors. In each of the samples illustrated in FIG. 9, the composition other than the area of the sensing layer (unit: L mm×W mm) is implemented the same. That is, the first sample 11 is implemented with a sensing layer 701 having an area of 2 mm×2 mm formed over an insulation layer 500 that is formed over the first electrode 310 and second electrode 320. For the second sample 12, the sensing layer 702 was implemented with an area of 2.5 mm×2.5 mm. For the third sample 13, the sensing layer 703 was implemented with an area of 3 mm×3 mm. For the fourth sample 14, the sensing layer 704 was implemented with an area of 3.5 mm×3.5 mm. For the fifth sample 15, the sensing layer 705 was implemented with an area of 4 mm×4 mm. For each sample, the graphene paste from which the sensing layer is implemented was formed by a screen printing technique, where the thickness of the graphene paste was 4 μm.

The initial capacitance values measured after applying power supplies having frequencies of 100 Hz, 1 kHz, and 10 kHz to each of the samples are represented in FIG. 10.

Looking at FIG. 10, it can be seen that the larger the area of the sensing layer included in the capacitive sensor, the higher is the initial capacitance value. It can also be seen that the lower the frequency of the power supply applied to the capacitive sensor, the higher the initial capacitance value. This trend is also observed in Table 1. Thus, it can be seen that, the larger the area of the sensing layer included in the capacitive sensor, and the lower the frequency of the power supply applied, the higher the initial capacitance value of the capacitive sensor.

While the spirit of the present solution has been described in detail with reference to specific embodiments, the embodiments are for illustrative purposes only and do not limit the invention. It is to be appreciated that many variations and equivalent embodiments can be derived by those skilled in the art without departing from the scope and spirit of the invention. The true technical scope of the invention is to be defined by the technical spirit disclosed in the appended claims.

What is claimed is:
1. A capacitive sensor comprising:
    a substrate comprising a terminal area and a sensing area;
    a first electrode comprising a first terminal disposed on the terminal area and a first pattern disposed on the sensing area;

a second electrode separated from the first electrode and comprising a second terminal disposed on the terminal area and a second pattern disposed on the sensing area;
an insulation layer disposed on the sensing area, the insulation layer covers the first pattern and the second pattern and exposes the first terminal and the second terminal; and
a sensing layer disposed on the insulation layer and covering at least a portion of the insulation layer such that the sensing layer is insulated and physically separated from the first and second electrodes,
wherein the sensing layer comprises a graphene.

2. The capacitive sensor of claim 1, wherein the substrate comprises silicon, glass, or alumina.

3. The capacitive sensor of claim 1, wherein the sensing layer is a graphene paste containing the graphene.

4. The capacitive sensor of claim 1, wherein the first electrode and the second electrode comprise at least one of chromium (Cr), gold (Au), aluminum (Al), platinum (Pt), molybdenum (Mo), copper (Cu), iron (Fe), tungsten (W), and palladium (Pd).

5. The capacitive sensor of claim 1, wherein the first pattern and the second pattern form an interdigitated pattern.

6. The capacitive sensor of claim 1, wherein a capacitance or a permittivity of the sensing layer changes according to a state of a measured substance touching the sensing layer.

7. The capacitive sensor of claim 1, wherein the sensing layer has a thickness of 4 μm to 6 μm.

8. The capacitive sensor of claim 1, wherein the insulation layer has a thickness of 500 A to 2000 A.

9. A method of manufacturing a capacitive sensor, the method comprising:
disposing at least one electrode comprising a terminal and a pattern on a substrate comprising a terminal area and a sensing area;
disposing an insulation layer on the sensing area of the substrate, the insulation layer covers the first pattern and the second pattern and exposes the first terminal and the second terminal; and
disposing a sensing layer on the insulation layer such that the sensing layer covers at least a portion of the insulation layer and is insulated and physically separated from the at least one electrode,
wherein the sensing layer comprises a graphene, and
wherein the terminal is disposed on the terminal area and the pattern is disposed on the sensing area.

10. The method of claim 9, wherein the forming of the at least one electrode comprises:
depositing an electrode substance; and
applying lithography, the lithography comprising coating a photosensitive material, exposure to light, and etching.

11. A method of manufacturing a capacitive sensor, the method comprising:
disposing at least one electrode comprising a terminal and a pattern on a substrate comprising a terminal area and a sensing area;
disposing an insulation layer on the sensing area of the substrate, the insulation layer covers the first pattern and the second pattern and exposes the first terminal and the second terminal; and
disposing a sensing layer on the insulation layer such that the sensing layer covers at least a portion of the insulation layer and is insulated and physically separated from the at least one electrode,
wherein the sensing layer comprises a graphene;
wherein the terminal is disposed on the terminal area and the pattern is disposed on the sensing area; and
wherein the disposing the sensing layer comprises: screen printing a graphene paste containing the graphene.

12. The capacitive sensor of claim 1, wherein the first pattern comprises a first extending part and a plurality of first branch parts, and the second pattern comprises a second extending part and a plurality of second branch parts.

13. The capacitative sensor of claim 12, wherein the plurality of first branch parts and the plurality of second branch parts form an interdigitated pattern.

* * * * *